(12) United States Patent
Gonnelli

(10) Patent No.: US 8,361,037 B2
(45) Date of Patent: Jan. 29, 2013

(54) MICRONEEDLES, MICRONEEDLE ARRAYS, AND SYSTEMS AND METHODS RELATING TO SAME

(75) Inventor: Robert R. Gonnelli, Mahwah, NJ (US)

(73) Assignee: Valeritas, Inc., Bridgewater, NJ (US)

( * ) Notice: Subject to any disclaimer, the term of this patent is extended or adjusted under 35 U.S.C. 154(b) by 0 days.

(21) Appl. No.: 10/251,480

(22) Filed: Sep. 19, 2002

(65) Prior Publication Data

US 2003/0135167 A1    Jul. 17, 2003

Related U.S. Application Data

(60) Provisional application No. 60/323,417, filed on Sep. 19, 2001.

(51) Int. Cl.
*A61M 5/00* (2006.01)
*A61M 5/32* (2006.01)
(52) U.S. Cl. .......................... 604/239; 604/272
(58) Field of Classification Search .............. 604/80, 604/85, 93.01, 173, 180, 183, 184, 187, 191, 604/192, 239, 258, 261, 272, 890.1; 424/449, 424/483
See application file for complete search history.

(56) References Cited

U.S. PATENT DOCUMENTS

| | | | |
|---|---|---|---|
| 2,817,336 A | 12/1957 | Kravitz et al. |
| 2,893,392 A | 7/1959 | Wagner et al. |
| 3,034,507 A | 5/1962 | McConnell et al. |
| 3,086,530 A | 4/1963 | Groom |
| 3,123,212 A | 3/1964 | Taylor et al. |
| 3,136,314 A | 6/1964 | Kravitz |
| 3,221,739 A | 12/1965 | Rosenthal |
| 3,221,740 A | 12/1965 | Rosenthal |
| 3,556,080 A | 1/1971 | Hein |
| 3,596,660 A | 8/1971 | Melone |
| 3,675,766 A | 7/1972 | Rosenthal |
| 3,682,162 A * | 8/1972 | Colyer .......................... 600/373 |
| 3,918,449 A | 11/1975 | Pistor |
| 3,964,482 A | 6/1976 | Gerstel et al. |
| 4,109,655 A | 8/1978 | Chacornac |
| 4,159,659 A | 7/1979 | Nightingale |
| 4,222,392 A | 9/1980 | Brennan |
| 4,320,758 A | 3/1982 | Eckenhoff et al. |
| 4,664,651 A | 5/1987 | Weinshenker et al. |
| 4,671,288 A | 6/1987 | Gough |
| 4,703,761 A | 11/1987 | Rathbone et al. |
| 4,771,660 A | 9/1988 | Yacowitz |
| 4,775,361 A | 10/1988 | Jacques et al. |

(Continued)

FOREIGN PATENT DOCUMENTS

| | | |
|---|---|---|
| DE | 19525607 | 1/1997 |
| EP | 0497620 B1 | 7/1998 |

(Continued)

OTHER PUBLICATIONS

Abrams, S.B. Versatile biosensor is compact and cheap. Biophotonics International 32-34 (Jan./Feb. 1998).

(Continued)

*Primary Examiner* — Kevin C Sirmons
*Assistant Examiner* — Andrew Gilbert
(74) *Attorney, Agent, or Firm* — Morse, Barnes-Brown & Pendleton, P.C.; Lisa M. Treannie, Esq.

(57) ABSTRACT

The microneedle devices disclosed herein in some embodiments include a substrate; one or more microneedles; and, optionally, a reservoir for delivery of drugs or collection of analyte, as well as pump(s), sensor(s), and/or microprocessor (s) to control the interaction of the foregoing.

30 Claims, 7 Drawing Sheets

U.S. PATENT DOCUMENTS

| | | | |
|---|---|---|---|
| 4,798,582 A | 1/1989 | Sarath et al. | |
| 4,832,682 A * | 5/1989 | Sarnoff | 604/21 |
| 4,837,049 A * | 6/1989 | Byers et al. | 216/6 |
| 4,921,475 A | 5/1990 | Sibalis | |
| 4,932,936 A | 6/1990 | Dykstra et al. | |
| 4,969,468 A | 11/1990 | Byers | |
| 5,035,711 A | 7/1991 | Aoki et al. | |
| 5,054,339 A | 10/1991 | Yacowitz | |
| 5,138,220 A | 8/1992 | Kirkpatrick | |
| 5,147,355 A | 9/1992 | Friedman et al. | |
| 5,250,023 A | 10/1993 | Lee et al. | |
| 5,279,544 A | 1/1994 | Gross et al. | |
| 5,279,552 A | 1/1994 | Magnet | |
| 5,335,670 A | 8/1994 | Fishman | |
| 5,364,374 A | 11/1994 | Morrison et al. | |
| 5,383,512 A | 1/1995 | Jarvis | |
| 5,401,242 A | 3/1995 | Yacowitz | |
| 5,457,041 A | 10/1995 | Ginaven et al. | |
| 5,527,288 A | 6/1996 | Gross et al. | |
| 5,549,644 A * | 8/1996 | Lundquist et al. | 604/22 |
| 5,582,184 A | 12/1996 | Erickson et al. | |
| 5,591,139 A | 1/1997 | Lin et al. | |
| 5,599,302 A | 2/1997 | Lilley et al. | |
| 5,605,662 A | 2/1997 | Heller et al. | |
| 5,611,806 A | 3/1997 | Jang | |
| 5,611,809 A | 3/1997 | Marshall et al. | |
| 5,611,942 A | 3/1997 | Mitsui et al. | |
| 5,618,295 A | 4/1997 | Min | |
| 5,632,957 A | 5/1997 | Heller et al. | |
| 5,658,515 A | 8/1997 | Lee et al. | |
| 5,697,901 A | 12/1997 | Eriksson | |
| 5,758,505 A | 6/1998 | Dobak et al. | |
| 5,801,057 A | 9/1998 | Smart | |
| 5,807,375 A | 9/1998 | Gross et al. | |
| 5,843,114 A | 12/1998 | Jang | |
| 5,848,991 A | 12/1998 | Gross et al. | |
| 5,852,495 A | 12/1998 | Parce | |
| 5,855,801 A * | 1/1999 | Lin et al. | 216/2 |
| 5,858,188 A | 1/1999 | Soane et al. | |
| 5,865,786 A | 2/1999 | Sibalis et al. | |
| 5,865,796 A | 2/1999 | McCabe | |
| 5,876,675 A | 3/1999 | Kennedy | |
| 5,879,326 A * | 3/1999 | Godshall et al. | 604/506 |
| 5,883,211 A | 3/1999 | Sassi et al. | |
| 5,885,211 A | 3/1999 | Eppstein et al. | |
| 5,899,880 A | 5/1999 | Bellhouse et al. | |
| 5,911,223 A | 6/1999 | Weaver et al. | |
| 5,919,159 A | 7/1999 | Lilley et al. | |
| 6,050,988 A | 4/2000 | Zuck | |
| 6,080,116 A | 6/2000 | Erickson et al. | |
| 6,113,722 A * | 9/2000 | Hoffman et al. | 156/155 |
| 6,132,755 A | 10/2000 | Eicher et al. | |
| 6,187,210 B1 * | 2/2001 | Lebouitz et al. | 216/11 |
| 6,219,574 B1 | 4/2001 | Cormier et al. | |
| 6,256,533 B1 * | 7/2001 | Yuzhakov et al. | 604/21 |
| 6,312,612 B1 | 11/2001 | Sherman et al. | |
| 6,334,856 B1 * | 1/2002 | Allen et al. | 604/191 |
| 6,440,118 B2 * | 8/2002 | Burr et al. | 604/503 |
| 6,451,240 B1 * | 9/2002 | Sherman et al. | 264/504 |
| 6,743,211 B1 | 6/2004 | Prausnitz et al. | |
| 7,060,192 B2 * | 6/2006 | Yuzhakov et al. | 216/11 |
| 2001/0053891 A1 | 12/2001 | Ackley | |
| 2002/0138049 A1 * | 9/2002 | Allen et al. | 604/272 |
| 2002/0185384 A1 * | 12/2002 | Leong et al. | 205/775 |
| 2002/0198512 A1 * | 12/2002 | Seward | 604/522 |

FOREIGN PATENT DOCUMENTS

| | | |
|---|---|---|
| EP | 0652600 B1 | 4/1999 |
| JP | 07132119 | 5/1995 |
| JP | 7196314 | 8/1995 |
| WO | WO 93/17754 | 9/1993 |
| WO | WO 96/37256 | 11/1996 |
| WO | WO 96/40365 | 12/1996 |
| WO | WO 96/41236 | 12/1996 |
| WO | WO 97/07734 | 3/1997 |
| WO | WO 98/00193 | 1/1998 |
| WO | WO 98/00194 | 1/1998 |
| WO | WO 98/28037 | 7/1998 |
| WO | WO 00/48669 | 8/2000 |
| WO | WO 00/74763 | 12/2000 |

OTHER PUBLICATIONS

Amsden. B.G. and Goosen, M.F.A. Transdermal Delivery of Peptide and Protein Drugs: an Overview. AIChE J. 41, 1972-1977 (Aug. 1995).

Brumlik, C.J. and Martin, C.R. Template Synthesis of Metal Microtubules. J. Am. Chem. Soc. 113, 3174-3175 (1991).

Chun, K. et al. Fabrication of Array of Hollow Microcapillaries Used for Injection of Genetic Materials into Animal/Plant Cells. Jpn. J. Appl. Phys. 38, 279-281 (1999).

Chun, K. et al. An Array of Hollow Microcapillaries for the Controlled Injection of Genetic Materials into Animal/Plant Cells.

Chun, K. et al. DNA Injection Into Plant Cell Conglomerates by Micromachined Hollow Microcapillary Arrays.

Clarke, M.S.F. and McNeil, P.L. Syringe loading introduces macromolecules into living mammalian cell cytosol. J. Cell. Sci. 102, 533-541 (1992).

Despont, M. et al. High-Aspect-Ratio, Ultrathick, Negative-Tone Near-UV Photoresist for MEMS Applications. IEEE 0-7803-3744-1/97 (1997).

Edell, D.J. et al. Factors Influencing the Biocompatibility of Insertable Silicon Microshafts in Cerebral Cortex. IEEE Transactions on Biomedical Engineering 39, 635-643 (1992).

Eleventh Annual International Workshop on Micro Electro Mechanical Systems, Heidelberg, Germany (Jan. 25-29, 1998). IEEE Catalog No. 98CH36176.

Frazier, A.B. and Allen, M.G. Metallic Microstructures Fabricated Using Photosensitive Polymide Electroplating Molds. J. Microelectromechanical Systems 2, 87-94 (Jun. 1993).

Frazier, A.B. et al. Two Dimensional Metallic Microelectrode Arrays for Extracellular Stimulation and Recording of Neurons. IEEE 0-7803-0957 pp. 195-200 (Feb. 1993).

Haga et al. Transdermal Iontophoretic delivery of insulin using a photoetched microdevice. J. Controlled Release 43, 139-149 (1997).

Hashmi, S. et al. Genetic Transformation of Nematodes Using Arrays of Micromechanical Piercing Structures. BioTechniques 19, 766-770 (Nov. 1995).

Henry et al. Microfabricated Microneedles: A Novel Method to Increase Transdermal Drug Delivery. J. Pharm. Sci. 87, 922-925 (1998).

Henry, S. et al. Micromachined Needles: A Novel Approach to Transdermal Drug Delivery. J. Pharm. Sci. 87, 922-925 (Aug. 1998).

Hoffert, S.P. Transcutaneous Methods Get Under the Skin. The Scientist 12, No. 16 (Aug. 17, 1998).

Infiltrator Intramural Drug Delivery: A New Generation of Drug Delivery Catheters from InterVentional Technologies, Inc., San Diego, CA (1997).

Jaeger, R.C. Introduction to Microelectronic Fabrication in the Addison-Wesley Modular Series on Solid State Devices, G.W. Neudeck and R.F. Pierret, eds. vol. 5, Addison-Wesley Publishing Co., Inc. (May 1993).

Jansen, H. et al. The Black Silicon Method IV: The Fabrication of Three-Dimensional Structures in Silicon with High Aspect Ratios for Scanning Probe Microscopy and Other Applications. MESA Res. Int, University of Twente, The Nethlerlands.

Laermer, F. et al. Bosch Deep Silicon Etching: Improving Uniformity and Etch Rate for Advanced MEMS Application. IEEE Catalog No. 99CH36291C, ISBN: 0-7803-5194-0 from the Twelfth IEEE International Conference on Micro Electro Mechanical Systems, Orlando FL, (Jan. 17-21, 1999).

Langer, R. Drug delivery and targeting. Nature 392 Supp, 5-10 (Apr. 30, 1998).

Lehmann, V. Porous Silicon—A New Material for MEMS. IEEE ISBN: 0-7803-2985-6/96 (1996).

Lin, L. et al. Silicon Processed Microneedles. The 7th International Conference on Solid-State Sensors and Actuators (1993).

Martin, C.R. et al. Template Synthesis of Organic Microtubules. J. Am. Chem. Soc. 112, 8976-8977 (1990).

Najafi, K. and Hetke, J.F. Strength Characterization of Silicon Microprobes in Neurophysiological Tissues. IEEE Transactions on Biomedical Engineering 37, 474-481 (May 1990).

101 Uses for Tiny Tubules. Science 247 (Mar. 23, 1990).

Percutaneous Absorption, R.L. Bronaugh and H.I. Maibach, eds. Marcel Dekker, Inc., New York (1989).

Prausnitz, M.R. Reversible Skin Permeabilization for Transdermal Delivery of Macromolecules. Critical Reviews in Therapeutic Drug Carrier Systems 14, 455-483 (1997).

Quan, M. Plasma etch yields microneedle arrays. Electronic Eng. Times, p. 63 (Jul. 13, 1996).

Reiss, S.M. Glucose- and Blood-Monitoring Systems Vie for Top Spot. Biophotonics International p. 43-46 (May/Jun. 1997).

Runyan, W.R. and Bean, K.E. Semiconductor Integrated Circuit Processing Technology, Addison-Wesley Publishing Co. (1990).

Schift, H. et al. Fabrication of replicated high precision insert elements for micro-optical bench arrangements. SPIE vol. 3513, p. 122-134 from SPIE Conference on Microelectronic Structures and MEMS for Optical Processing IV, Santa Clara (Sep. 1998).

Single-crystal whiskers. Biophotonics Int'l, p. 64 (Nov./Dec. 1996).

Talbot, N.H. and Pisano, A.P. Polymolding: Two Wafer Polysilicon Micromolding of Closed-Flow Passages for Microneedles and Microfluidic Devices. Solid-State Sensor and Actuator Workshop, Hilton Head Island, SC (Jun. 8-11, 1998).

Transdermal Drug Delivery, J. Hadgraft and R.H. Guy, eds. Marcel Dekker, Inc., New York (1989).

Trimmer, W. et al. Injection of DNA into Plant and Animal Tissues with Micromechanical Piercing Structures. IEEE Catalog No. 95CH35754, ISBN: 0-7803-2503-6 from Micro Electro Mechanical Systems, Amsterdam p. 111-115 (1995).

Weber, L. et al. Micro molding—a powerful tool for the large scale production of precise microstructures. SPIE No. 0-8194-2277-0/96, vol. 2879, p. 156-167 (1996).

Zuska, P. Microtechnology Opens Doors to the Universe of Small Space. MD&DI (1997).

* cited by examiner

MICRONEEDLES, MICRONEEDLE ARRAYS, AND SYSTEMS AND METHODS RELATING TO SAME

REFERENCE TO RELATED APPLICATIONS

This application claims priority to U.S. Ser. No. 60/323,417 filed Sep. 19, 2001, entitled MICRONEEDLE, and naming Robert R. Gonnelli as inventor, the contents of which are hereby incorporated by reference.

TECHNICAL FIELD

The invention relates microneedles, microneedle arrays, and systems and methods relating to same.

BACKGROUND

Microneedles can be used, for example, to sample analyte content of a subject (e.g., a human) and/or to delivery a medicament (e.g., a drug) to a subject (e.g., a human).

Topical delivery of drugs is a very useful method for achieving systemic or localized pharmacological effects. The main challenge in transcutaneous drug delivery is providing sufficient drug penetration across the skin. The skin consists of multiple layers starting with a stratum cornuem layer about (for humans) twenty (20) microns in thickness (comprising dead cells), a viable epidermal tissue layer about seventy (70) microns in thickness, and a dermal tissue layer about two (2) mm in thickness.

The thin layer of stratum corneum represents a major barrier for chemical penetration through skin. The stratum corneum is responsible for 50% to 90% of the skin barrier property, depending upon the drug material's water solubility and molecular weight. The epidermis comprises living tissue with a high concentration of water. This layer presents a lesser barrier for drug penetration. The dermis contains a rich capillary network close to the dermal/epidermal junction, and once a drug reaches the dermal depth it diffuses rapidly to deep tissue layers (such as hair follicles, muscles, and internal organs), or systemically via blood circulation.

Current topical drug delivery methods are based upon the use of penetration enhancing methods, which often cause skin irritation, and the use of occlusive patches that hydrate the stratum corneum to reduce its barrier properties. Only small fractions of topically applied drug penetrates through skin, with very poor efficiency.

Conventional methods of biological fluid sampling and non-oral drug delivery are normally invasive. That is, the skin is lanced in order to extract blood and measure various components when performing fluid sampling, or a drug delivery procedure is normally performed by injection, which causes pain and requires special medical training.

Alternatives to drug delivery by injection are known. One alternative is disclosed in U.S. Pat. No. 3,964,482 (by Gerstel), in which an array of either solid or hollow microneedles is used to penetrate through the stratum corneum, into the epidermal layer, but not to the dermal layer.

The use of microneedles has great advantages in that intracutaneous drug delivery can be accomplished without pain and without bleeding. Microneedles are sufficiently long to penetrate through the stratum corneum skin layer and into the epidermal layer, yet are also sufficiently short to not penetrate to the dermal layer. Of course, if the dead cells have been completely or mostly removed from a portion of skin, then a very minute length of microneedle could be used to reach the viable epidermal tissue Although microneedle technology shows much promise for drug delivery, it would be a further advantage if a microneedle apparatus could be provided to sample fluids within skin tissue.

SUMMARY

In general, the systems and methods described herein relate to microneedles, microneedle arrays, and systems and methods relating to same. Accordingly, it is a primary advantage of the invention to provide a microneedle array which can perform intracutaneous drug delivery. It is another advantage of the invention to provide a microneedle array that can perform interstitial body-fluid testing and/or sampling. It is a further advantage of the invention to provide a microneedle array as part of a closed-loop system to control drug delivery, based on feedback information that analyzes body fluids, which can achieve real-time continuous dosing and monitoring of body activity. It is yet another advantage of the invention to provide an iontophoretically/microneedle-enhanced transdermal drug delivery system in order to achieve high-rate drug delivery and to achieve sampling of body fluids. It is a yet further advantage of the invention to provide a method for manufacturing an array of microneedles using microfabrication techniques, including known semiconductor fabrication techniques. It is still another advantage of the invention to provide a method of manufacturing an array of microneedles comprising a plastic material by a "self-molding" method, a micromolding method, a microembossing method, or a microinjection method.

In one aspect, the invention features a microneedle that includes first, second and third materials. The first material is in the shape of a microneedle and has first and second sides. The second material is disposed adjacent the first side of the first material, and the third metal is disposed adjacent the second side of the first material.

The first material can be an electrically insulating material. The electrically insulating material can be, for example, air, silicon, glass, plastic, ceramic and/or mylar, and oxidized silicon.

The second material can be an electrically conductive material. The electrically conductive material can be, for example, a metal or an alloy. The electrically conductive material can be, for example, gold, silver, copper, tantalum, tin, aluminum, platinum, palladium, nickel, titanium or an alloy thereof.

The third material can be an electrically conductive material. The electrically conductive material can be, for example, metal or an alloy. The electrically conductive material can be, for example, gold, silver, copper, tantalum, tin, aluminum, platinum, palladium, nickel, titanium or an alloy thereof.

The second and third materials may be the same or different, and can be biologically compatible metals.

The microneedle can further include a layer of an electron transfer agent (e.g., on the surface of the second and/or third materials). The electron transfer agent can be an enzyme which interacts with an analyte, such as an analyte present in a subject (e.g., a human). One example of an electron transfer agent is glucose oxidase. Other examples are set forth herein.

In another aspect, the invention features a system that includes one of the microneedles in electrical communication with a sensor. The sensor can measure a change in an electrical parameter, such as capacitance, inductance, or resistance. In optional embodiments, the sensor measures change is a magnetic parameter or an optical characteristic.

In a further aspect, the invention features a method of making one of the microneedles. The method can include, for example, one or more microfabrication steps. In one aspect, the invention features a microneedle array that includes a substrate and a plurality of microneedles connected to the substrate. At least one of the microneedles includes first, second and third materials. The first material is in the shape of a microneedle and has first and second sides. The second material is disposed adjacent the first side of the first material, and the third metal is disposed adjacent the second side of the first material.

In a further aspect, the invention features a method of making one of the microneedle arrays. The method can include, for example, one or more microfabrication steps.

In certain embodiments, microneedles, microneedle arrays, and/or microneedle systems can be involved in delivering drugs. For example, a system can include a sample section and a delivery section. The sections can be in communication so that the delivery section delivers one or more desired medicaments in response to a signal from the sample section. Optionally, a does control system may be employed to select or regulate a delivered dose based, at least in part, on a change in an electrical, magnetic or optical parameter.

BRIEF DESCRIPTION OF THE DRAWINGS

The foregoing and other objects and advantages of the invention will be appreciated more fully from the following further description thereof, with reference to the accompanying drawings wherein.

DETAILED DESCRIPTION

Figure 1:
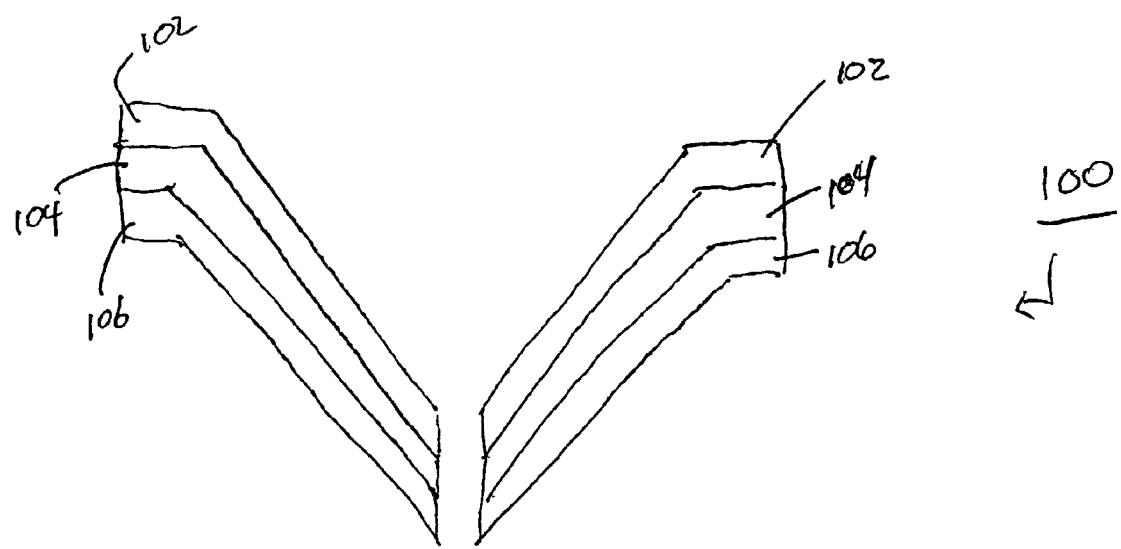
FIG. 1 is a cross-sectional view of an embodiment of a microneedle.

To provide an overall understanding of the invention, certain illustrative embodiments will now be described, including a microneedle, and microneedle system that detects the presence of a biological compound or concentration of a biological compound of interest. However, it will be understood by one of ordinary skill in the art that the systems and methods described herein can be adapted and modified for other suitable applications and that such other additions and modifications will not depart from the scope hereof.

The devices disclosed herein are useful in transport of material into or across biological barriers including the skin (or parts thereof); the blood-brain barrier; mucosal tissue (e.g., oral, nasal, ocular, vaginal, urethral, gastrointestinal, respiratory); blood vessels; lymphatic vessels; or cell membranes (e.g., for the introduction of material into the interior of a cell or cells). The biological barriers can be in humans or other types of animals, as well as in plants, insects, or other organisms, including bacteria, yeast, fungi, and embryos.

The microneedle devices can be applied to tissue internally with the aid of a catheter or laparoscope. For certain applications, such as for drug delivery to an internal tissue, the devices can be surgically implanted.

The microneedle device disclosed herein is typically applied to skin. The stratum corneum is the outer layer, generally between 10 and 50 cells, or between 10 and 20 µm thick. Unlike other tissue in the body, the stratum corneum contains "cells" (called keratinocytes) filled with bundles of cross-linked keratin and keratohyalin surrounded by an extracellular matrix of lipids. It is this structure that is believed to give skin its barrier properties, which prevents therapeutic transdermal administration of many drugs. Below the stratum corneum is the viable epidermis, which is between 50 and 100 µm thick. The viable epidermis contains no blood vessels, and it exchanges metabolites by diffusion to and from the dermis. Beneath the viable epidermis is the dermis, which is between 1 and 3 mm thick and contains blood vessels, lymphatics, and nerves.

The microneedle devices disclosed herein in some embodiments include a substrate; one or more microneedles; and, optionally, a reservoir for delivery of drugs or collection of analyte, as well as pump(s), sensor(s), and/or microprocessor (s) to control the interaction of the foregoing.

The substrate of the device can be constructed from a variety of materials, including metals, ceramics, semiconductors, organics, polymers, and composites. The substrate includes the base to which the microneedles are attached or integrally formed. A reservoir may also be attached to the substrate.

The microneedles of the device can be constructed from a variety of materials, including metals, ceramics, semiconductors, organics, polymers, and composites. Preferred materials of construction include pharmaceutical grade stainless steel, gold, titanium, nickel, iron, gold, tin, chromium, copper, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polymethacrylic acid, ethylenevinyl acetate, polytetrafluorethylene and polyesters.

Generally, the microneedles should have the mechanical strength to remain intact for delivery of drugs, and to serve as a conduit for the collection of biological fluid and/or tissue, while being inserted into the skin, while remaining in place for up to a number of days, and while being removed. In certain embodiments, the microneedles maybe formed of biodegradable polymers. However, for these embodiments that employ biodegratable materials, the mechanical requirement may be less stringent.

The microneedles can be formed of a porous solid, with or without a sealed coating or exterior portion, or hollow. As used herein, the term "porous" means having pores or voids throughout at least a portion of the microneedle structure, sufficiently large and sufficiently interconnected to permit passage of fluid and/or solid materials through the microneedle. As used herein, the term "hollow" means having one or more substantially annular bores or channels through the interior of the microneedle structure, having a diameter sufficiently large to permit passage of fluid and/or solid materials through the microneedle. The annular bores may extend throughout all or a portion of the needle in the direction of the tip to the base, extending parallel to the direction of the needle or branching or exiting at a side of the needle, as appropriate. A solid or porous microneedle can be hollow. One of skill in the art can select the appropriate porosity and/or bore features required for specific applications. For example, one can adjust the pore size or bore diameter to permit passage of the particular material to be transported through the microneedle device.

The microneedles can have straight or tapered shafts. A hollow microneedle that has a substantially uniform diameter, which needle does not taper to a point, is referred to herein as a "microtube." As used herein, the term "microneedle" includes, although is not limited to both microtubes and tapered needles unless otherwise indicated. In a preferred embodiment, the diameter of the microneedle is greatest at the base end of the microneedle and tapers to a point at the end distal the base. The microneedle can also be fabricated to have a shaft that includes both a straight (untapered) portion and a tapered portion.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The shaft can have one or more bores. The cross-sectional dimensions typically are between about 10 nm and 1 mm, preferably between 1 micron and 200 microns, and more preferably between 10 and 100 µm. The outer diameter is typically between about 10 µm and about 100 µm, and the inner diameter is typically between about 3 µm and about 80 µm.

The length of the microneedles typically is between about 1 and 1 mm, preferably between 10 microns and 500 microns, and more preferably between 30 and 200 µm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles.

The microneedles can be oriented perpendicular or at an angle to the substrate. Preferably, the microneedles are oriented perpendicular to the substrate so that a larger density of microneedles per unit area of substrate can be provided. An array of microneedles can include a mixture of microneedle orientations, heights, or other parameters.

In a preferred embodiment of the device, the substrate and/or microneedles, as well as other components, are formed from flexible materials to allow the device to fit the contours of the biological barrier, such as the skin, vessel walls, or the eye, to which the device is applied. A flexible device will facilitate more consistent penetration during use, since penetration can be limited by deviations in the attachment surface. For example, the surface of human skin is not flat due to dermatoglyphics (i.e. tiny wrinkles) and hair.

The microneedle device may include a reservoir in communication with the microneedles. The reservoir can be attached to the substrate by any suitable means. In a preferred embodiment, the reservoir is attached to the back of the substrate (opposite the microneedles) around the periphery, using an adhesive agent (e.g., glue). A gasket may also be used to facilitate formation of a fluid-tight seal.

In one embodiment, the reservoir contains drug, for delivery through the microneedles. The reservoir may be a hollow vessel, a porous matrix, or a solid form including drug which is transported therefrom. The reservoir can be formed from a variety of materials that are compatible with the drug or biological fluid contained therein. Preferred materials include natural and synthetic polymers, metals, ceramics, semiconductors, organics, and composites.

The microneedle device can include one or a plurality of chambers for storing materials to be delivered. In the embodiment having multiple chambers, each can be in fluid connection with all or a portion of the microneedles of the device array. In one embodiment, at least two chambers are used to separately contain drug (e.g., a lyophilized drug, such as a vaccine) and an administration vehicle (e.g., saline) in order to prevent or minimize degradation during storage. Immediately before use, the contents of the chambers are mixed. Mixing can be triggered by any means, including, for example, mechanical disruption (i.e. puncturing or breaking), changing the porosity, or electrochemical degradation of the walls or membranes separating the chambers. In another embodiment, a single device is used to deliver different drugs, which are stored separately in different chambers. In this embodiment, the rate of delivery of each drug can be independently controlled.

In a preferred embodiment, the reservoir is in direct contact with the microneedles and have holes through which drug could exit the reservoir and flow into the interior of hollow or porous microneedles. In another preferred embodiment, the reservoir has holes which permit the drug to transport out of the reservoir and onto the skin surface. From there, drug is transported into the skin, either through hollow or porous microneedles, along the sides of solid microneedles, or through pathways created by microneedles in the skin.

The microneedle device also must be capable of transporting material across the barrier at a useful rate. For example, the microneedle device must be capable of delivering drug across the skin at a rate sufficient to be therapeutically useful. The device may include a housing with microelectronics and other micromachined structures to control the rate of delivery either according to a preprogrammed schedule or through active interface with the patient, a healthcare professional, or a biosensor. The rate can be controlled by manipulating a variety of factors, including the characteristics of the drug formulation to be delivered (e.g., its viscosity, electric charge, and chemical composition); the dimensions of each microneedle (e.g., its outer diameter and the area of porous or hollow openings); the number of microneedles in the device; the application of a driving force (e.g., a concentration gradient, a voltage gradient, a pressure gradient); and the use of a valve.

The rate also can be controlled by interposing between the drug in the reservoir and the opening(s) at the base end of the microneedle polymeric or other materials selected for their diffusion characteristics. For example, the material composition and layer thickness can be manipulated using methods known in the art to vary the rate of diffusion of the drug of interest through the material, thereby controlling the rate at which the drug flows from the reservoir through the microneedle and into the tissue.

Transportation of molecules through the microneedles can be controlled or monitored using, for example, various combinations of valves, pumps, sensors, actuators, and microprocessors. These components can be produced using standard manufacturing or microfabrication techniques. Actuators that may be useful with the microneedle devices disclosed herein include micropumps, microvalves, and positioners. In a preferred embodiment, a microprocessor is programmed to control a pump or valve, thereby controlling the rate of delivery.

Flow of molecules through the microneedles can occur based on diffusion, capillary action, or can be induced using conventional mechanical pumps or nonmechanical driving forces, such as electroosmosis or electrophoresis, or convection. For example, in electroosmosis, electrodes are positioned on the biological barrier surface, one or more microneedles, and/or the substrate adjacent the needles, to create a convective flow which carries oppositely charged ionic species and/or neutral molecules toward or into the biological barrier. In a preferred embodiment, the microneedle device is used in combination with another mechanism that enhances the permeability of the biological barrier, for example by increasing cell uptake or membrane disruption, using electric fields, ultrasound, chemical enhancers, viruses, pH, heat and/or light.

Passage of the microneedles, or drug to be transported via the microneedles, can be manipulated by shaping the microneedle surface, or by selection of the material forming the microneedle surface (which could be a coating rather than the microneedle per se). For example, one or more grooves on the outside surface of the microneedles can be used to direct the passage of drug, particularly in a liquid state. Alternatively, the physical surface properties of the microneedle could be manipulated to either promote or inhibit transport of material along the microneedle surface, such as by controlling hydrophilicity or hydrophobicity.

The flow of molecules can be regulated using a wide range of valves or gates. These valves can be the type that are selectively and repeatedly opened and closed, or they can be single-use types. For example, in a disposable, single-use drug delivery device, a fracturable barrier or one-way gate may be installed in the device between the reservoir and the opening of the microneedles. When ready to use, the barrier can be broken or gate opened to permit flow through the microneedles. Other valves or gates used in the microneedle devices can be activated thermally, electrochemically, mechanically, or magnetically to selectively initiate, modulate, or stop the flow of molecules through the needles. In a preferred embodiment, flow is controlled by using a rate-limiting membrane as a "valve."

The microneedle devices can further include a flowmeter or other dose control system to monitor flow and optionally control flow through the microneedles and to coordinate use of the pumps and valves.

Useful sensors may include sensors of pressure, temperature, chemicals, and/or electromagnetic fields. Biosensors can be employed, and in one arrangement, are located on the microneedle surface, inside a hollow or porous microneedle, or inside a device in communication with the body tissue via the microneedle (solid, hollow, or porous). These microneedle biosensors may include any suitable transducers, including but not limited to potentiometric, amperometric, optical, magnetic and physiochemical. An amperometric sensor monitors currents generated when electrons are exchanged between a biological system and an electrode. Blood glucose sensors frequently are of this type. As described herein, the sensors may be formed to sense changes resulting from an election transfer agent interacting with analyte or analytes of interest.

The microneedle may function as a conduit for fluids, solutes, electric charge, light, or other materials. In one embodiment, hollow microneedles can be filled with a substance, such as a gel, that has a sensing functionality associated with it. In an application for sensing based on binding to a substrate or reaction mediated by an enzyme, the substrate or enzyme can be immobilized in the needle interior, which would be especially useful in a porous needle to create an integral needle/sensor.

Wave guides can be incorporated into the microneedle device to direct light to a specific location, or for dection, for example, using means such as a pH dye for color evaluation. Similarly, heat, electricity, light or other energy forms may be precisely transmitted to directly stimulate, damage, or heal a specific tissue or intermediary (e.g., tattoo remove for dark skinned persons), or diagnostic purposes, such as measurement of blood glucose based on IR spectra or by chromatographic means, measuring a color change in the presence of immobilized glucose oxidase in combination with an appropriate substrate.

A collar or flange also can be provided with the device, for example, around the periphery of the substrate or the base. It preferably is attached to the device, but alternatively can be formed as integral part of the substrate, for example by forming microneedles only near the center of an "oversized" substrate. The collar can also emanate from other parts of the device. The collar can provide an interface to attach the microneedle array to the rest of the device, and can facilitate handling of the smaller devices.

In a preferred embodiment, the microneedle device includes an adhesive to temporarily secure the device to the surface of the biological barrier. The adhesive can be essentially anywhere on the device to facilitate contact with the biological barrier. For example, the adhesive can be on the surface of the collar (same side as microneedles), on the surface of the substrate between the microneedles (near the base of the microneedles), or a combination thereof.

FIG. 1 depicts one microneedle 100 that is generally is between about 1 µm and 1 mm in length. The diameter and length both affect pain as well as functional properties of the needles. In transdermal applications, the "insertion depth" of the microneedle is preferably less than about 200 µm, more preferably about 30 µm, so that insertion of the microneedles into the skin through the stratum corneum does not penetrate past the epidermis into the dermis, thereby avoiding contacting nerves and reducing the potential for causing pain. In such applications, the actual length of the microneedles may be longer, since the portion of the microneedles distal the tip may not be inserted into the skin; the uninserted length depends on the particular device design and configuration. The actual (overall) height or length of microneedles should be equal to the insertion depth plus the uninserted length. In applications where the microneedle 100 is employed to sample blood or tissue, the length of the microneedle is selected to allow sufficient penetration for blood to flow into the microneedle or the desired tissue be penetrated.

More particularly, FIG. 1 is a cross-sectional view of an embodiment of a microneedle 100 formed of three layers of material 102, 104 and 106.

In certain embodiments, layer 102 is an electrically conductive material, such as a metal or an alloy. Examples of metals and alloy constituents that can be used in layer 102 include, for example, transition metals and the like. In some embodiments, layer 102 is formed of gold, platinum, palladium, nickel, titanium or a combination thereof.

In some embodiments, layer 104 is formed of an electrically insulating material. Materials useful as non-conductive members include, but are not limited to, silicon, glass, plastic, ceramic and mylar.

In certain embodiments, layer 106 is formed of an electrically conductive material, such as a metal or an alloy. Examples of metals and alloy constituents that can be used in layer 102 include, for example, transition metals and the like. In some embodiments, layer 106 is formed of gold, platinum, palladium, nickel, titanium or a combination thereof. In general, layer 102 is formed of a different material than layer 106. For example, in embodiments in which layer 102 is formed of gold, layer 106 can be formed of platinum. As another example, in embodiments in which layer 102 is formed of platinum, layer 106 can be formed of gold.

Figure 2:
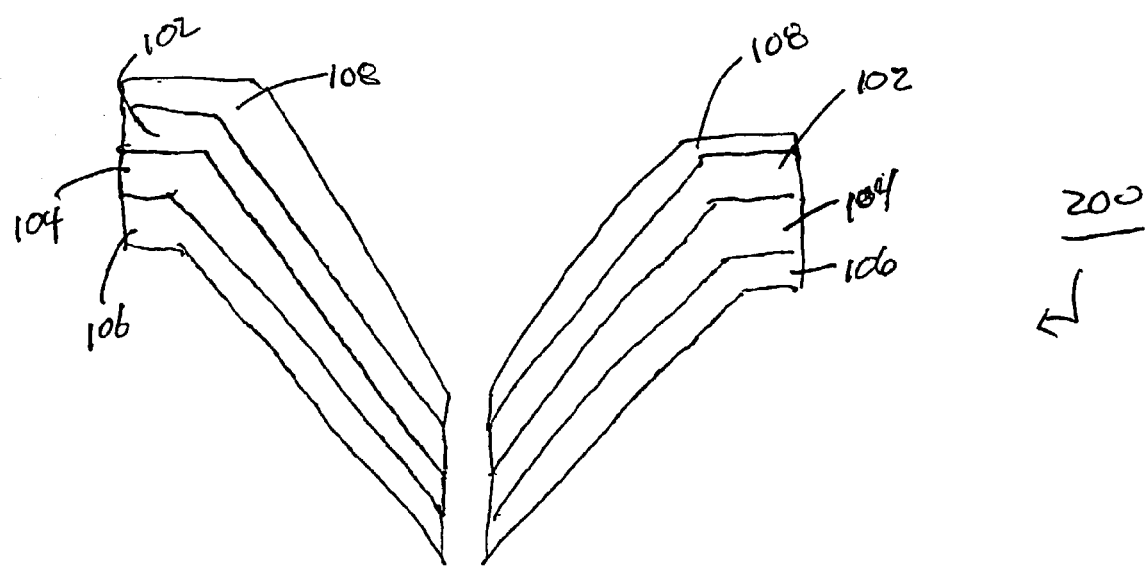
FIG. 2 is a cross-sectional view of an embodiment of a microneedle.

FIG. 2 shows an embodiment of a microneedle 200 including layers 102, 104,106 and a layer 108 of an electron transfer agent. Examples of electron transfer agents include enzymes, and functional derivatives thereof.

Electron transfer agents can be selected, for example, from among those that participate in one of several organized electron transport systems in vivo. Examples of such systems include respiratory phosphorylation that occurs in mitochondria and the primary photosynthetic process of thyrakoid membranes.

An electron transfer agent can specifically interact with a metabolite or analyte in the patient's system. For example, electron transfer agent-analyte pairs can include antibody-antigen and enzyme-member.

Redox enzymes, such as oxidases and dehydrogenases, can be particularly useful in the device. Examples of such enzymes are glucose oxidase (EC 1.1.3.4), lactose oxidase, galactose oxidase, enoate reductase, hydrogenase, choline dehydrogenase, alcohol dehydrogenase (EC 1.1.1.1), and glucose dehydrogenase.

Devices described herein can exhibit specificity for a given analyte; and the specificity can be imparted by the selective interaction of an analyte (e.g., glucose) with the electron transfer agent (e.g., glucose oxidase or glucose dehydrogenase).

Figure 3A:
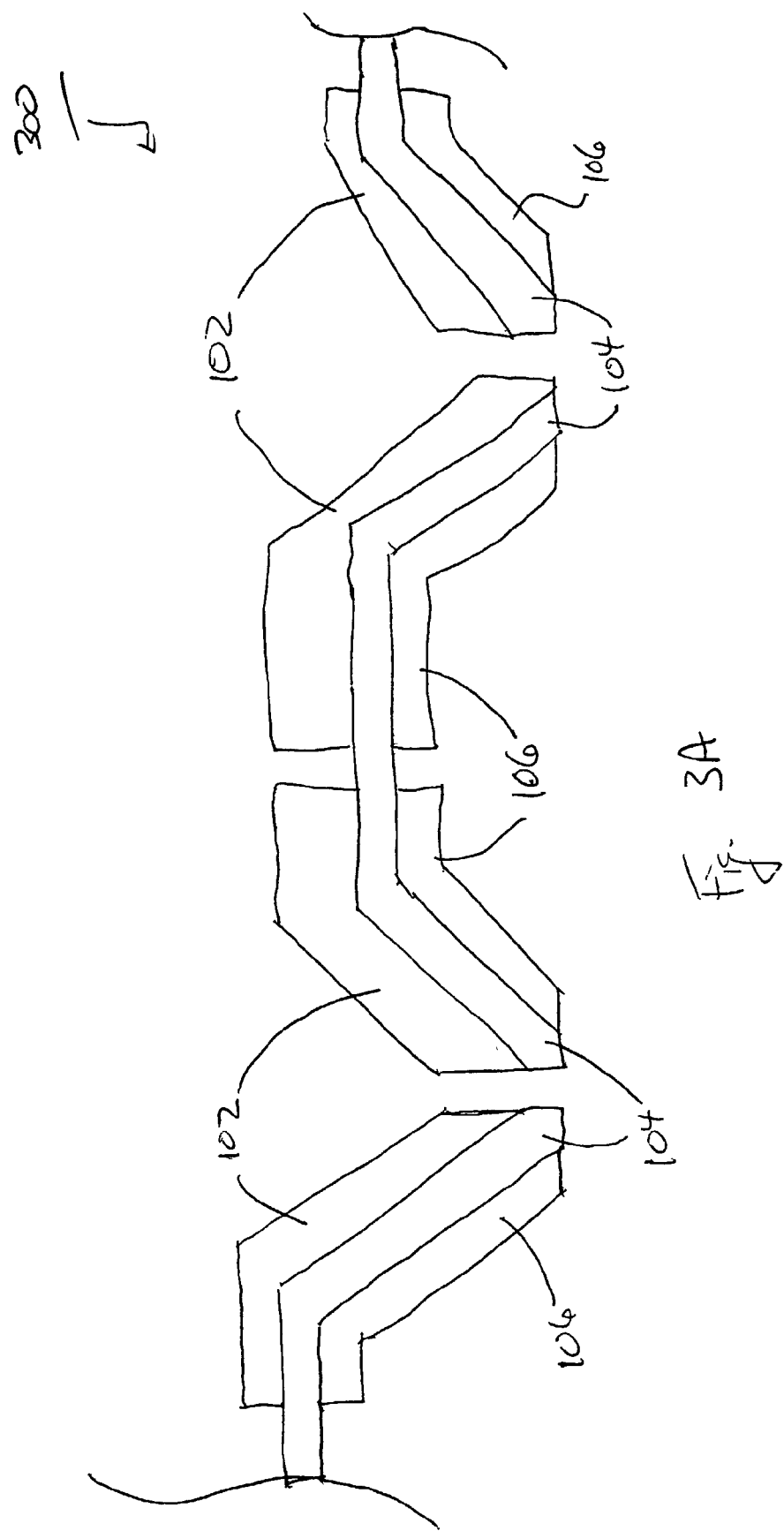
FIGS. 3A and 3B are cross-sectional and top views, respectively, of an embodiment of an array of microneedles.
Figure 3B:
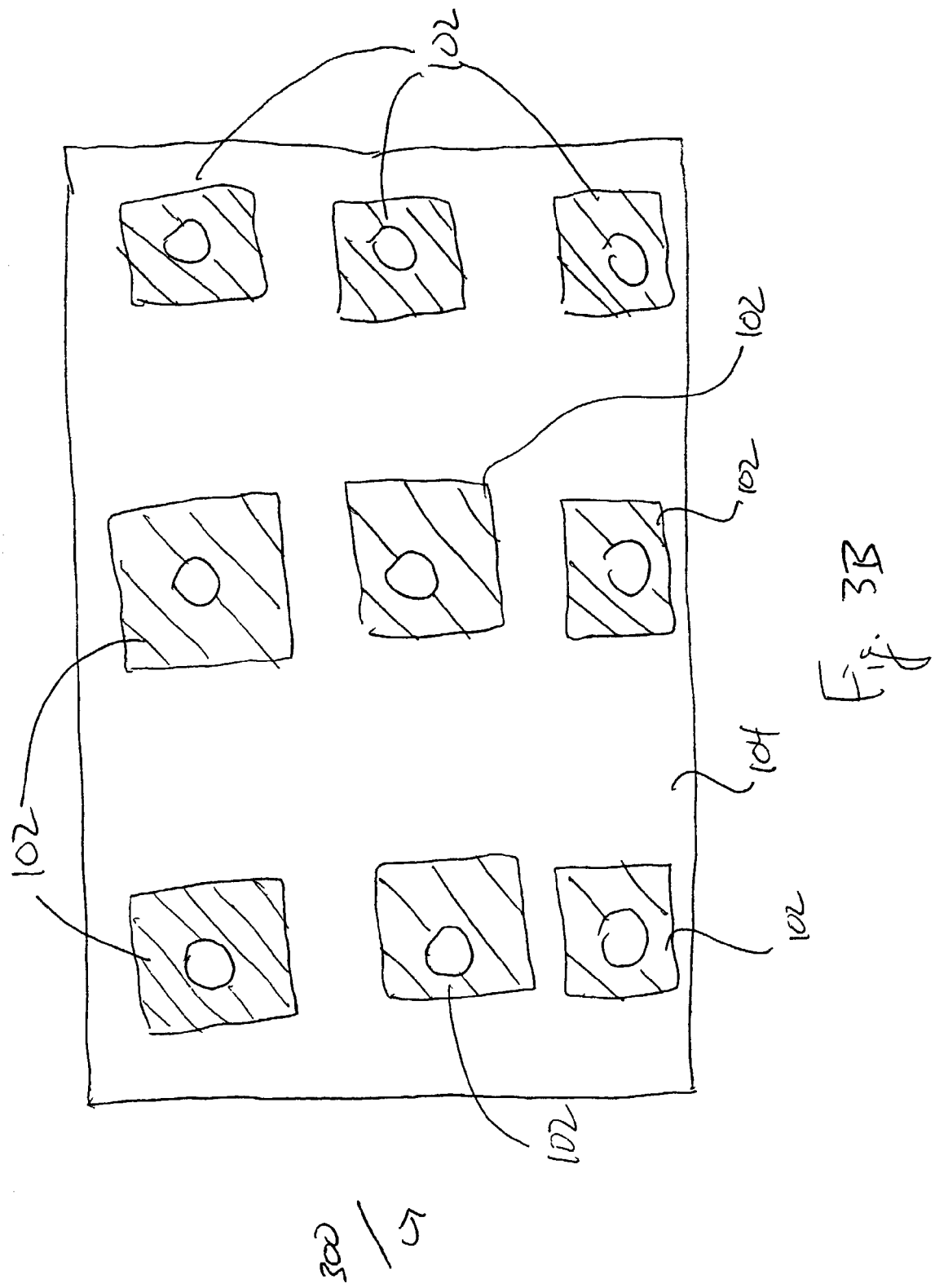

FIGS. 3A and 3B show an embodiment of a microneedle array 300 in which layers (e.g., electrically conducting layers) 102 and 106 are discontinuous. Although shown in these figures as being discontinuous, the invention is not so limited. For example, layers 102 and/or 106 can be continuously disposed over the entire surface of layer 104 (e.g., a substrate). Moreover, the pattern of layers 102 and/or 106 can be varied as desired.

Figure 4A:
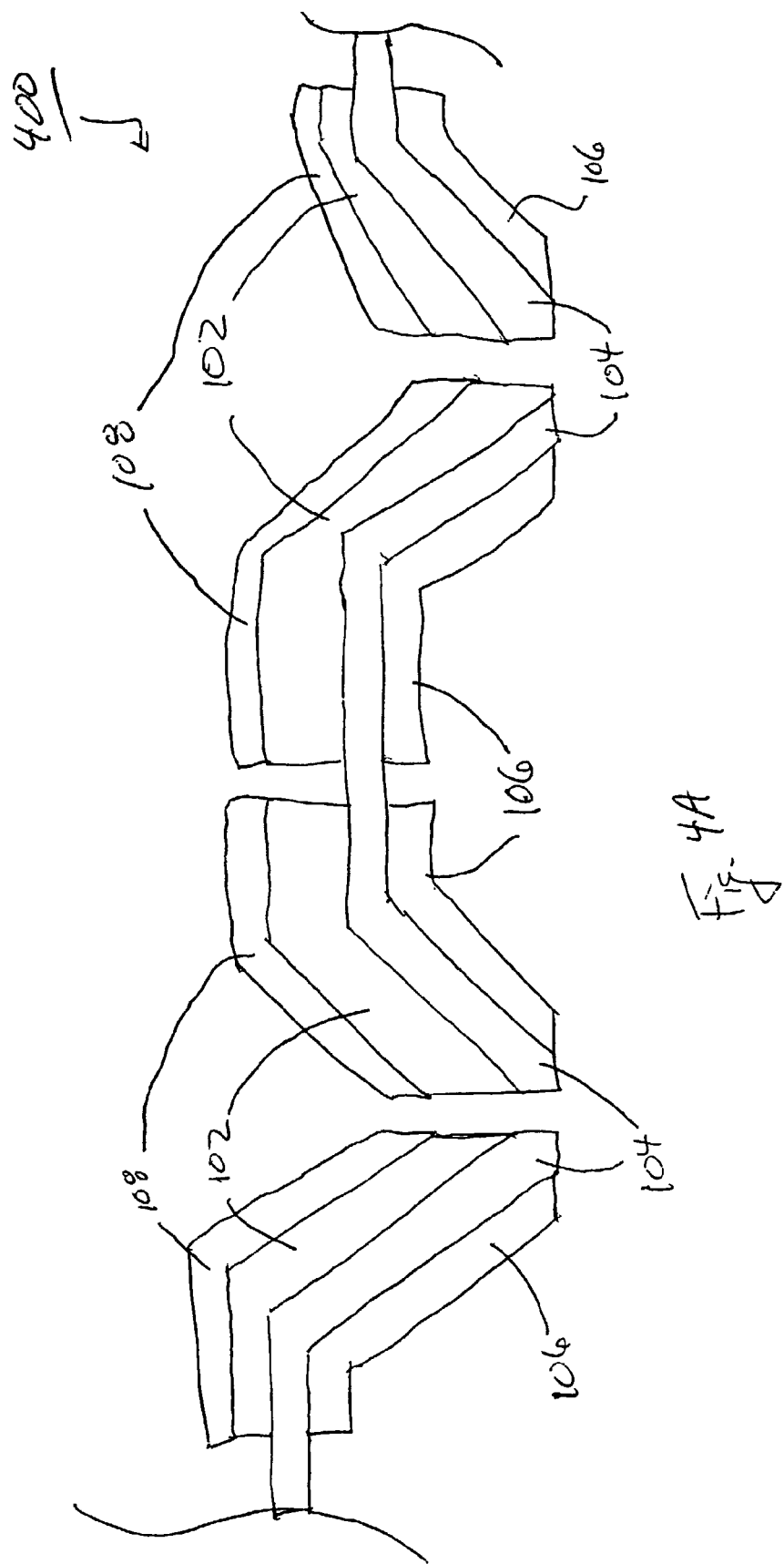
FIGS. 4A and 4B are cross-sectional and top views, respectively, of an embodiment of an array of microneedles.
Figure 4B:
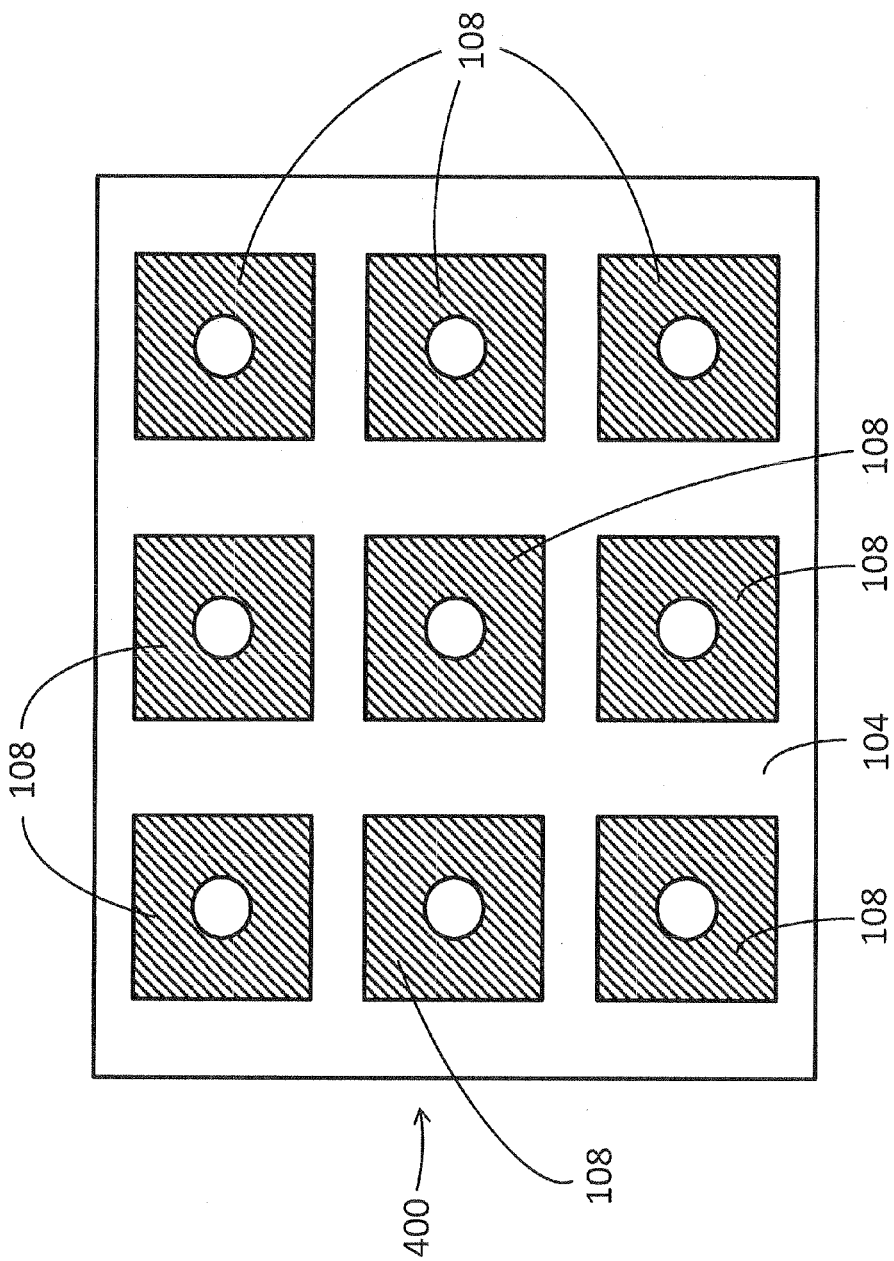

FIGS. 4A and 4B show an embodiment of a microneedle array 400 in which layers (e.g., electrically conducting layers) 102 and 106, and an electron transfer agent layer 108 are discontinuous. Although shown in these figures as being discontinuous, the invention is not so limited. For example, layers 102, 106 and/or 108 can be continuously disposed over the entire surface of layer 104 (e.g., a substrate). Moreover, the pattern of layers 102, 106 and/or 108 can be varied as desired.

The sensing device can be used to detect any interaction which changes the charge, pH, or conformation of a given agent-analyte pair. Such agent-analyte pairs include, without limitation, protein-protein pairs, protein-small organic molecule pairs, or small organic molecule-small organic molecule pairs. Interactions between any of the foregoing agent-analyte pairs which result in a change in the charge, pH, and/or conformation of either the agent and/or the analyte are useful in the methods of the present invention.

Examples of agent-analyte pairs, wherein the interaction between the agent and the analyte results in a change in the charge, pH, and/or conformation of either the agent or the analyte include the addition of one or more phosphate groups (phosphorylation) to a substrate by a kinase. Such a phosphorylation event results in a change in the charge of the phosphorylated protein, and this change in phosphorylation may alter the conformation of that protein. Kinases are involved in a cell proliferation, differentiation, migration, and regulation of the cell cycle. Misregulation of kinase activity, either an increase or decrease in activity, is implicated in cancer and other proliferative disorders such as psoriasis.

In addition to the activity of kinases which phosphorylate target proteins, phosphatases change the charge and/or conformation of a target substrate by removing one or more phosphate groups (dephosphorylation) from a target substrate. The activity of phosphatases are also critical in regulation of the cell cycle, regulation of cell proliferation, cell differentiation, and cell migration. Misregulation of phosphatase activity, either an increase or decrease in activity, is implicated in proliferative disorders including many forms of cancers.

Further examples of agent-analyte interactions useful in the methods of the present invention include receptor-ligand interactions which result in changes in conformation of either the receptor of the ligand. Growth factors including, without limitation, fibroblast growth factor (FGF), epidermal growth factor (EGF), platlet derived growth factor (PDGF), nerve derived growth factor (NGF) modulate cellular behavior via interaction with cell surface receptors. The interaction with the cell surface receptor results in the activation of signal transduction pathways which result in changes in cellular behavior. In the case of growth factors, these changes in cellular behavior include changes in cell survival, changes in cell proliferation, and changes in cell migration. The interaction between the growth factor and its receptor results in a change in conformation, and often a change in phosphorylation, of the receptor and/or the growth factor itself. This change could be readily detected by the methods of the present invention.

Further examples of biological and biochemical processes which can be readily detected by the methods of the present invention include interactions which alter the post translation modification of a protein. Post translation modification which alter the activity of a protein include changes in glycosylation state, lipophilic modification, acetylation, and phosphorylation of a protein. The addition of subtraction of one or more sugar moieties, acetyl groups, or phosphoryl groups not only affects the activity of the protein, but also affects the charge, pH and/or conformation of the protein.

Agent-analyte pairs may also include the interaction of an antibody which specifically detects a given protein of interest with that protein of interest. Antibody-protein interactions may be extremely specific, and are used to detect low concentration of proteins (e.g., ELIZA assays). In this way, the methods of the present invention can be used to detect a low level of any protein of interest which may be elevated in a fluid sample.

Agent-analyte pairs may also include interactions between a protein and a small organic molecule or between small organic molecules. For example, the methods of the present invention can be used to detect changes in the level of sugar (e.g., glucose, lactose, galactose, etc.) lipid, amino acid or cholesterol, in a fluid sample of a patient. A variety of conditions result in changes in the levels of small organic molecules in body fluids of a patient. These include diabetes, hypoglycemia, hypolipidemia, hyperlipidemia, hypercholesterolemia, PKU, hypothyroidism, hyperthyroidism, and other metabolic disorders which alter the bodies ability to metabolize sugars, lipids, and/or proteins.

In certain embodiments, a microneedle or microneedle array as described herein can be used in a device designed to qualitatively and/or quantitatively measure an analyte in a subject (e.g., a human). In such embodiments, layer 106 can act as a reference electrode while layer 102 (in conjunction with, layer 108) can act as a working electrode, and layers 102 and 106 can be in electrical communication with a sensor. Generally, in such embodiments, layers 102 and 106 are electrically isolated from each other (e.g., by forming layer 104 of an electrically insulating material).

Methods of manufacturing, as well as various design features and methods of using, the microneedles and microneedle arrays described herein are disclosed, for example, in Published PCT patent application WO 99/64580, entitled "Microneedle Devices and Methods of Manufacture and Use Thereof," Published PCT patent application WO 00/74763, entitled "Devices and Methods for Enhanced Microneedle Penetration or Biological Barriers," Published PCT patent application WO 01/49346, entitled "Stacked Microneedle Systems," and Published PCT patent application WO 00/48669, entitled "Electroactive Pore," each of which is hereby incorporated by reference. Generally, the microneedles and microneedles arrays can be prepared using electrochemical etching techniques, plasma etching techniques, electroplating techniques and microfabrication techniques. Typically, layer 104 (e.g., substrate 104) is prepared using an appropriate technique, and layers 106 and 102 are subsequently formed (e.g, by an appropriate deposition technique, such as a vapor deposition technique or an electroplating technique). Layer 108 can be applied using, for example, standard techniques.

Figure 5:
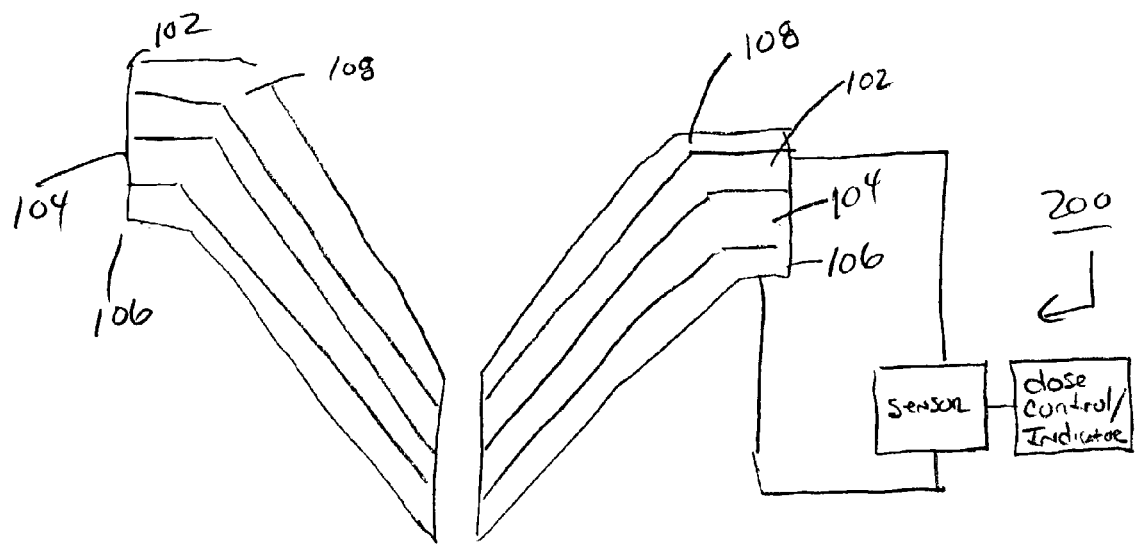
FIG. 5 depicts one embodiment of a sample collection systems according to the invention that employs a sensor for detecting the presence of one or more analytes.

FIG. 5 depicts the microneedle 200 of FIG. 2 with a sensor electrically coupled between the metal layer 102 and the metal layer 106. The sensor can be suitable sensor capable of measuring or detecting a change in an electrical parameter, such as voltage, current, capacitance, resistance and/or inductance. The sensor may comprise a resistor, differential amplifier, capacitance meter or any other suitable device. In the embodiment of FIG. 5 the sensor measures changes in an electrical parameter, but is other embodiments, the sensor may be capable of measuring a magnetic parameter, such as a hall effect device, or an optical characteristic. The sensor may generate a signed capable of operating a dose control system or flow meter that controls or allows the flow of a drug to the patient. Optionally, the sensor may control an alarm or indicator that may be visual, or auditory.

In embodiments, microneedles, microneedle arrays, and/or microneedle systems can be involved in delivering drugs. For example, a system can include a sample section and a delivery section. The sections can be in communication so that the delivery section delivers one or more desired medicaments in response to a signal from the sample section.

The device may be used for single or multiple uses for rapid transport across a biological barrier or may be left in place for longer times (e.g., hours or days) for long-term transport of molecules. Depending on the dimensions of the device, the application site, and the route in which the device is introduced into (or onto) the biological barrier, the device may be used to introduce or remove molecules at specific locations.

As discussed above, FIG. 1 shows a side elevational view of a schematic of a preferred embodiment of the microneedle device 10 in a transdermal application. The device 10 is applied to the skin such that the microneedles 12 penetrate through the stratum corneum and enter the viable epidermis so that the tip of the microneedle at least penetrates into the viable epidermis. In a preferred embodiment, drug molecules in a reservoir within the upper portion 11 flow through or around the microneedles and into the viable epidermis, where the drug molecules then diffuse into the dermis for local treatment or for transport through the body.

To control the transport of material out of or into the device through the microneedles, a variety of forces or mechanisms can be employed. These include pressure gradients, concentration gradients, electricity, ultrasound, receptor binding, heat, chemicals, and chemical reactions. Mechanical or other gates in conjunction with the forces and mechanisms described above can be used to selectively control transport of the material.

In particular embodiments, the device should be "user-friendly." For example, in some transdermal applications, affixing the device to the skin should be relatively simple, and not require special skills. This embodiment of a microneedle may include an array of microneedles attached to a housing containing drug in an internal reservoir, wherein the housing has a bioadhesive coating around the microneedles. The patient can remove a peel-away backing to expose an adhesive coating, and then press the device onto a clean part of the skin, leaving it to administer drug over the course of, for example, several days.

Essentially any drug or other bioactive agents can be delivered using these devices. Drugs can be proteins, enzymes, polysaccharides, polynucleotide molecules, and synthetic organic and inorganic compounds. A preferred drug is insulin. Representative agents include anti-infectives, hormones, growth regulators, drugs regulating cardiac action or blood flow, and drugs for pain control. The drug can be for local treatment or for regional or systemic therapy. The following are representative examples, and disorders they are used to treat: Calcitonin, osteoporosis; Enoxaprin, anticoagulant; Etanercept, rheumatoid arthritis; Erythropoietin, anemia; Fentanyl, postoperative and chronic pain; Filgrastin, low white blood cells from chemotherapy; Heparin, anticoagulant; Insulin, human, diabetes; Interferon Beta I a, multiple sclerosis; Lidocaine, local anesthesia; Somatropin, growth hormone; Sumatriptan, and migraine headaches.

In this way, many drugs can be delivered at a variety of therapeutic rates. The rate can be controlled by varying a number of design factors, including the outer diameter of the microneedle, the number and size of pores or channels in each microneedle, the number of microneedles in an array, the magnitude and frequency of application of the force driving the drug through the microneedle and/or the holes created by the microneedles. For example, devices designed to deliver drug at different rates might have more microneedles for more rapid delivery and fewer microneedles for less rapid delivery. As another example, a device designed to deliver drug at a variable rate could vary the driving force (e.g., pressure gradient controlled by a pump) for transport according to a schedule which was preprogrammed or controlled by, for example, the user or his doctor. The devices can be affixed to the skin or other tissue to deliver drugs continuously or intermittently, for durations ranging from a few seconds to several hours or days.

One of skill in the art can measure the rate of drug delivery for particular microneedle devices using in vitro and in vivo methods known in the art. For example, to measure the rate of transdermal drug delivery, human cadaver skin mounted on standard diffusion chambers can be used to predict actual rates. See Hadgraft & Guy, eds., Transdermal Drug Delivery: Developmental Issues and Research Initiatives (Marcel Dekker, New York 1989); Bronaugh & Maibach, Percutaneous Absorption, Mechanisms—Methodology—Drug Delivery (Marcel Dekker, New York 1989). After filling the compartment on the dermis side of the diffusion chamber with saline, a microneedle array is inserted into the stratum corneum; a drug solution is placed in the reservoir of the microneedle device; and samples of the saline solution are taken over time and assayed to determine the rates of drug transport.

In an alternate embodiment, biodegradable or non-biodegradable microneedles can be used as the entire drug delivery device, where biodegradable microneedles are a preferred embodiment. For example, the microneedles may be formed of a biodegradable polymer containing a dispersion of an active agent for local or systemic delivery. The agent could be released over time, according to a profile determined by the composition and geometry of the microneedles, the concentration of the drug and other factors. In this way, the drug reservoir is within the matrix of one or more of the microneedles.

In another alternate embodiment, these microneedles may be purposefully sheared off from the substrate after penetrating the biological barrier. In this way, a portion of the microneedles would remain within or on the other side of the biological barrier and a portion of the microneedles and their substrate would be removed from the biological barrier. In the case of skin, this could involve inserting an array into the skin, manually or otherwise breaking off the microneedles tips and then remove the base of the microneedles. The portion of the microneedles which remains in the skin or in or across another biological barrier could then release drug over time according to a profile determined by the composition and geometry of the microneedles, the concentration of the drug and other factors. In a preferred embodiment, the microneedles are made of a biodegradable polymer. The release of drug from the biodegradable microneedle tips could be controlled by the rate of polymer degradation. Microneedle tips could release drugs for local or systemic effect, but could also release other agents, such as perfume, insect repellent and sun block.

Microneedle shape and content could be designed to control the breakage of microneedles. For example, a notch could be introduced into microneedles either at the time of fabrication or as a subsequent step. In this way, microneedles would preferentially break at the site of the notch. Moreover, the size and shape of the portion of microneedles which break off could be controlled not only for specific drug release patterns, but also for specific interactions with cells in the body. For example, objects of a few microns in size are known to be taken up by macrophages. The portions of microneedles that break off could be controlled to be bigger or smaller than that to prevent uptake by macrophages or could be that size to promote uptake by macrophages, which could be desirable for delivery of vaccines.

One embodiment of the devices described herein may be used to remove material from the body across a biological barrier, i.e. for minimally invasive diagnostic sensing. For example, fluids can be transported from interstitial fluid in a tissue into a reservoir in the upper portion of the device. The fluid can then be assayed while in the reservoir or the fluid can be removed from the reservoir to be assayed, for diagnostic or other purposes. For example, interstitial fluids can be removed from the epidermis across the stratum corneum to assay for glucose concentration, which should be useful in aiding diabetics in determining their required insulin dose. Other substances or properties that would be desirable to detect include lactate (important for athletes), oxygen, pH, alcohol, tobacco metabolites, and illegal drugs (important for both medical diagnosis and law enforcement).

The sensing device can be in or attached to one or more microneedles, or in a housing adapted to the substrate. Sensing information or signals can be transferred optically (e.g., refractive index) or electrically (e.g., measuring changes in electrical impedance, resistance, current, voltage, or combination thereof). For example, it may be useful to measure a change as a function of change in resistance of tissue to an electrical current or voltage, or a change in response to channel binding or other criteria (such as an optical change) wherein different resistances are calibrated to signal that more or less flow of drug is needed, or that delivery has been completed.

In one embodiment, one or more microneedle devices can be used for (1) withdrawal of interstitial fluid, (2) assay of the fluid, and/or (3) delivery of the appropriate amount of a therapeutic agent based on the results of the assay, either automatically or with human intervention. For example, a sensor delivery system may be combined to form, for example, a system which withdraws bodily fluid, measures its glucose content, and delivers an appropriate amount of insulin. The sensing or delivery step also can be performed using conventional techniques, which would be integrated into use of the microneedle device. For example, the microneedle device could be used to withdraw and assay glucose, and a conventional syringe and needle used to administer the insulin, or vice versa.

In an alternate embodiment, microneedles may be purposefully sheared off from the substrate after penetrating the biological barrier, as described above. The portion of the microneedles which remain within or on the other side of the biological barrier could contain one or more biosensors. For example, the sensor could change color as its output. For microneedles sheared off in the skin, this color change could be observed through the skin by visual inspection or with the aid of an optical apparatus.

Other than transport of drugs and biological molecules, the microneedles may be used to transmit or transfer other materials and energy forms, such as light, electricity, heat, or pressure. The microneedles, for example, could be used to direct light to specific locations within the body, in order that the light can directly act on a tissue or on an intermediary, such as light-sensitive molecules in photodynamic therapy. The microneedles can also be used for aerosolization or delivery for example directly to a mucosal surface in the nasal or buccal regions or to the pulmonary system.

The microneedle devices disclosed herein also should be useful for controlling transport across tissues other than skin. For example, microneedles could be inserted into the eye across, for example, conjunctiva, sclera, and/or cornea, to facilitate delivery of drugs into the eye. Similarly, microneedles inserted into the eye could facilitate transport of fluid out of the eye, which may be of benefit for treatment of glaucoma. Microneedles may also be inserted into the buccal (oral), nasal, vaginal, or other accessible mucosa to facilitate transport into, out of, or across those tissues. For example, a drug may be delivered across the buccal mucosa for local treatment in the mouth or for systemic uptake and delivery. As another example, microneedle devices may be used internally within the body on, for example, the lining of the gastrointestinal tract to facilitate uptake of orally-ingested drugs or the lining of blood vessels to facilitate penetration of drugs into the vessel wall. For example, cardiovascular applications include using microneedle devices to facilitate vessel distension or immobilization, similarly to a stent, wherein the microneedles/substrate can function as a "staple-like" device to penetrate into different tissue segments and hold their relative positions for a period of time to permit tissue regeneration. This application would be particularly useful with biodegradable devices. These uses may involve invasive procedures to introduce the microneedle devices into the body or could involve swallowing, inhaling, injecting or otherwise introducing the devices in a non-invasive or minimally-invasive manner.

Those skilled in the art will know or be able to ascertain using no more than routine experimentation, many equivalents to the embodiments and practices described herein.

Accordingly, it will be understood that the invention is not to be limited to the embodiments disclosed herein, but is to be understood from the following claims, which are to be interpreted as broadly as allowed under the law.

The invention claimed is:

1. A microneedle device, comprising
 a first layer formed into the shape of a microneedle and comprising a first material suitable for piercing tissue,
 a continuous second layer disposed on and internal to the first layer and capable of acting as an electrical insulator, and
 a continuous third layer disposed on and internal to the second layer and capable of conducting electrical charge, wherein said microneedle has a length of between about 10 microns and 1 mm and permits passage of fluid and/or solid materials through the microneedle, and wherein the second layer is continuously disposed over the entire first layer.

2. A microneedle according to claim 1, wherein the first layer comprises a metal material.

3. A microneedle according to claim 2, wherein the metal material is selected from the group consisting of: copper, silver, tungsten, gold, platinum, palladium, nickel and titanium.

4. A microneedle according to claim 1, wherein the second layer comprises an electrically insulating material.

5. A microneedle according to claim 4, wherein the insulating material is selected from the group consisting of silicon, glass, plastic, air ceramic, oxidized silicon and mylar.

6. A microneedle according to claim 1, wherein the third layer comprises a metal.

7. A microneedle according to claim 6, wherein the metal is selected from the group consisting of copper, silver, tungsten, gold, platinum, palladium, nickel and titanium.

8. A microneedle according to claim 1, wherein at least one of the second and third layers comprises material deposited onto the first layer.

9. A microneedle according to claim 1, wherein at least one of the layers comprises layers formed of a doped material.

10. A microneedle according to claim 1, wherein at least one of the layers comprises a layer formed of sputtered material.

11. A microneedle according to claim 1, further comprising a layer having an electron transfer agent.

12. A microneedle according to claim 1, wherein the electron transfer agent comprises an enzyme.

13. A microneedle device according to claim 1, wherein the first layer and the continuous third layer are coupled to a sensor for detecting a change in an electrical parameter that is caused at least in part by delivery of an agent.

14. A microneedle device according to claim 1, wherein the microneedle comprises the sensor to which the first layer and the continuous third layer are coupled.

15. A microneedle according to claim 1, further comprising an agent, wherein the agent is disposed on the third layer and further wherein the agent comprises an agent for activating a detectable change in an electrical parameter upon delivery into or across the biological barrier.

16. A method for withdrawing a third material from across a biological barrier, comprising withdrawing the third material with the microneedle device of claim 1.

17. The method of claim 16, wherein the third material is an interstitial fluid from a tissue.

18. The method of claim 17, wherein the interstitial fluid is removed from the epidermis across the stratum corneum for assaying concentration of glucose, lactate, oxygen, pH, alcohol, tobacco metabolites, or illegal drugs.

19. The method of claim 16, wherein the microneedle is sheared off the microneedle device after penetrating the biological barrier and withdrawing the material.

20. A method for transporting a second material into or across a biological barrier, comprising
delivering the second material with a microneedle device comprising a first layer formed into the shape of a microneedle and comprising a first material suitable for piercing tissue, a continuous second layer disposed on and internal to the first layer and capable of acting as an electrical insulator, and a continuous third layer disposed on and internal to the second layer and capable of conducting electrical charge, wherein said microneedle has a length of between about 10 microns and 1 mm and permits passage of fluid and/or solid materials through the microneedle, and wherein the second layer is continuously disposed over the entire first layer.

21. The method of claim 20, wherein the biological barrier is skin, blood-brain barrier, mucosal tissue, blood vessel, lymphatic vessel, cell membrane, eye, conjunctiva, sclera, cornea, lining of the gastrointestinal tract, or lining of the blood vessels.

22. The method of claim 20, wherein the biological barrier is in a human, a non-human animal, a plant, an insect, a bacterium, a yeast, a fungus, or an embryo.

23. The method of claim 20, wherein the microneedle device is applied to the biological barrier internally with the aid of a catheter or laproscope.

24. The method of claim 20, wherein the microneedle device is surgically implanted.

25. The method of claim 20, wherein the second material comprises a bioactive agent selected from proteins, enzymes, polysaccharides, polynucleotide molecules, and synthetic organic and inorganic compounds.

26. The method of claim 20, wherein the second material comprises insulin.

27. The method of claim 20, wherein the second material comprises anti-infectives, hormones, growth regulators, anti-coagulants, drugs regulating cardiac action or blood flow, and drugs for pain control.

28. The method of claim 20, wherein the second material is useful to treat: osteoporosis; rheumatoid arthritis; anemia; postoperative and chronic pain; low white blood cell counts resulting from chemotherapy; diabetes; multiple sclerosis; local anesthesia; and migraine headaches.

29. The method of claim 20, wherein the second material is delivered as a variety of therapeutically useful rates.

30. The method of claim 20, wherein the microneedle is sheared off the microneedle device after penetrating the biological barrier and transporting the material.

* * * * *